US00PP32283P2

(12) United States Plant Patent
Van Swieten

(10) Patent No.: US PP32,283 P2
(45) Date of Patent: Oct. 6, 2020

(54) ***PHALAENOPSIS* ORCHID PLANT NAMED 'PHALHITWOQ'**

(50) Latin Name: ***Phalaenopsis* hybrid**
Varietal Denomination: PHALHITWOQ

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/873,012

(22) Filed: Jan. 15, 2020

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62
See application file for complete search history.

(56) References Cited

PUBLICATIONS

UPOV hit to a *Phalaenopsis* plant named 'PHALHITWOQ', QZ PBR 20182455, filed Sep. 25, 2018.*

* cited by examiner

*Primary Examiner* — Anne Marie Grunberg
(74) *Attorney, Agent, or Firm* — Jondle & Associates, P.C.

(57) ABSTRACT

A new and distinct variety of *Phalaenopsis* plant named 'PHALHITWOQ', particularly characterized by having reddish-purple flowers with very light purple edges and red-purple lips, a moderately compressed to medium petal shape, lips with a depth of 30.0 mm to 32.0 mm, and is propagated by meristem tissue culture, is disclosed.

3 Drawing Sheets

Genus and species: *Phalaenopsis* hybrid.
Variety denomination: 'PHALHITWOQ'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALHITWOQ'.

The new *Phalaenopsis* plant is a product of a planned breeding program conducted by the inventor in Bleiswijk, the Netherlands. The objective of this breeding program was to create a new *Phalaenopsis* plant with numerous attractive, large reddish-purple flowers with very light purple edges and red-purple lips, suitable for potted plant production.

The new *Phalaenopsis* plant 'PHALHITWOQ' is a result of cross-pollination made by the inventor in December 2007 in Bleiswijk, the Netherlands, of the proprietary female, or seed parent, *Phalaenopsis* hybrid '32522-04' (unpatented) with the proprietary male, or pollen parent, *Phalaenopsis* hybrid '32522-03' (unpatented).

The new *Phalaenopsis* was selected by the inventor as a single plant within the progeny of the stated cross-pollination in a controlled greenhouse in Bleiswijk, the Netherlands, in December 2010. Asexual reproduction of the new *Phalaenopsis* plant by meristem tissue culture since 2016 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Sep. 25, 2018, by Applicant who obtained the subject matter disclosed directly from the inventor. 'PHALHITWOQ' has not been made publicly available or sold anywhere in the world prior to the effective filing date of this application with the exception of sales or disclosures made one year or less before the effective filing date of this claimed invention by Applicant who obtained 'PHALHITWOQ' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALHITWOQ' as a new and distinct variety of *Phalaenopsis* plant:

1) Reddish-purple flowers with very light purple edges and red-purple lips;
2) Moderately compressed to medium petal shape; and
3) Lips with a depth of 30.0 mm to 32.0 mm.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in November 2019. Colors in the photographs may differ from the color values cited in the detailed botanical description, which accurately describe the actual colors of the new variety.

DESCRIPTION OF THE NEW VARIETY

Figure 1:
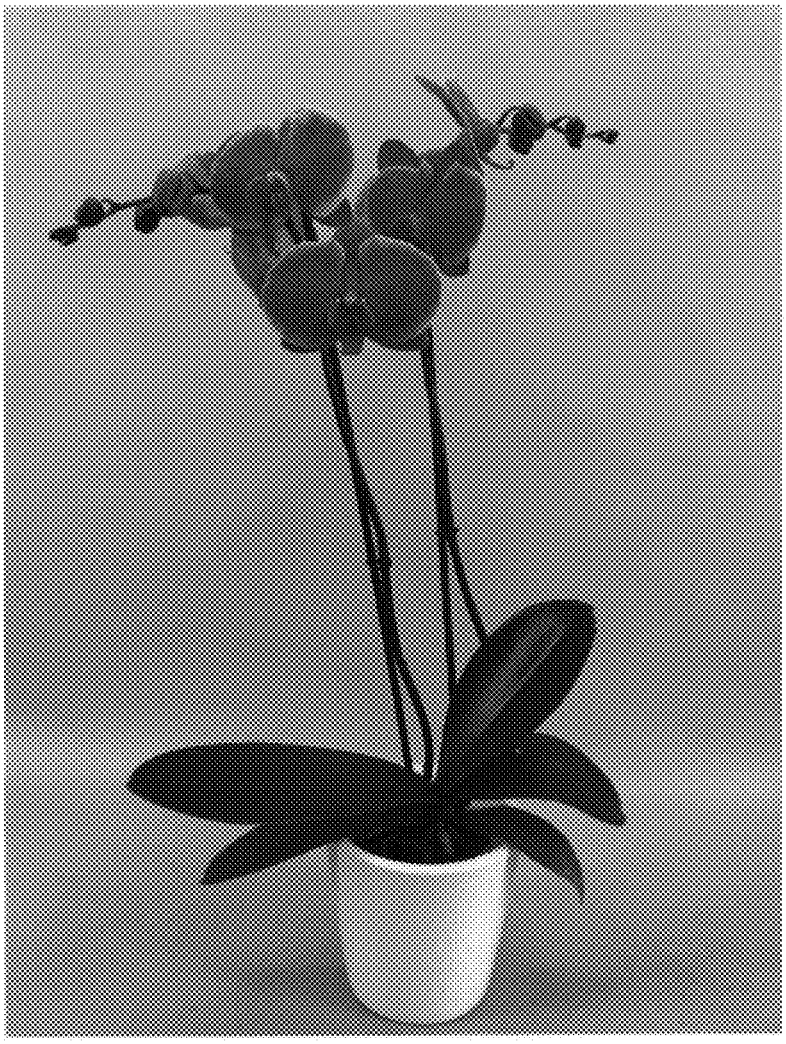
FIG. 1 shows the overall plant habit, including blooms, buds, and foliage of 'PHALHITWOQ'.
Figure 2:
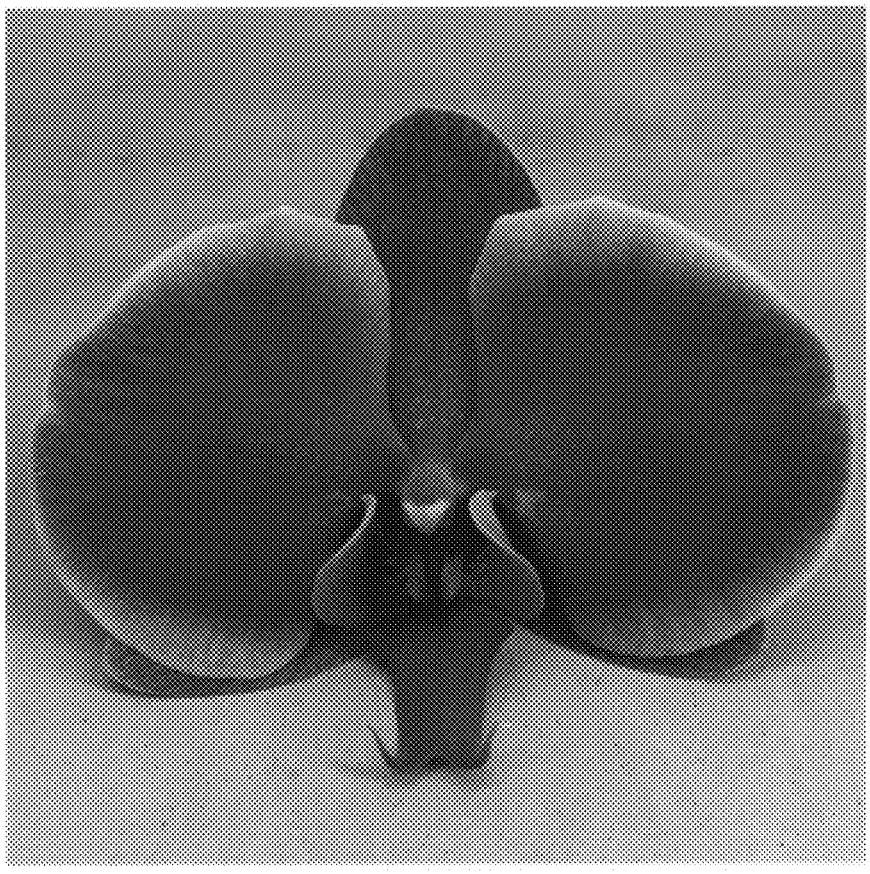
FIG. 2 shows a close-up of a flower of 'PHALHITWOQ'.
Figure 3:
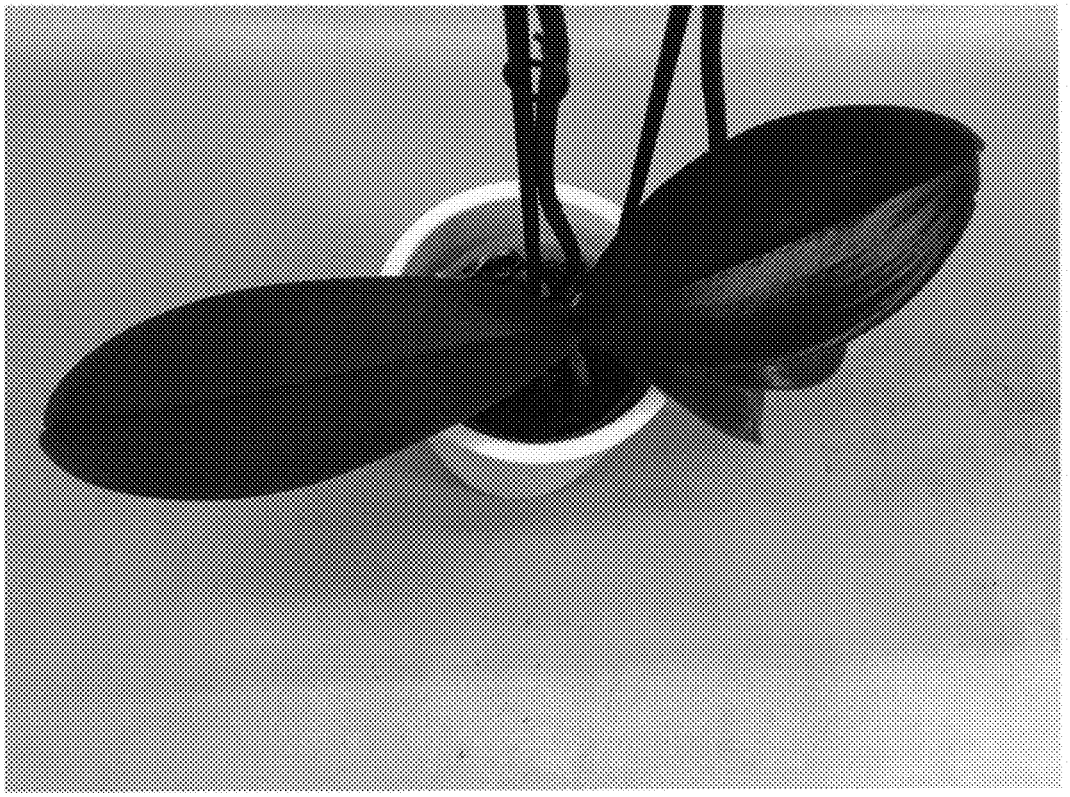
FIG. 3 shows an overhead view of the leaves of 'PHALHITWOQ'.

The following detailed description sets forth the distinctive characteristics of 'PHALHITWOQ'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in November 2019 on flowering plants which were planted in 12-centimeter (diameter) pots. After in-vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALHITWOQ'.

Parentage:

*Female parent*.—*Phalaenopsis* cultivar '32522-04' (unpatented).

*Male parent*.—*Phalaenopsis* cultivar '32522-03' (unpatented).

Propagation:

*Type*.—Meristem tissue culture.

Roots:

*Root description*.—Greyed-green (between RHS 190B and 190C) colored roots with branching lateral roots having purplish-red (RHS N77B) colored root tips.

Plant:

*Commercial crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendant with raceme or panicle inflorescence.

*Height* (*from soil level to top of inflorescence*).—Approximately 55.0 cm to 60.0 cm.

*Width* (*measured from leaf tips*).—About 32.0 cm to 34.0 cm.

*Vigor*.—Strong.

Leaves:

*Mature leaves*.—Quantity per plant: 6 to 8 leaves are produced before flowering. Length (fully expanded): 17.0 cm to 20.0 cm. Width: 7.5 cm to 8.5 cm. Position of the broadest part of the leaf: Toward the apex. Shape: Obovate. Base shape: Moderately elongated. Apex: Obtuse unequal. Leaf blade angle with the petiole (measured from the horizontal position): Between 15 degrees and 35 degrees. Leaf margin: Entire. Color: Upper surface: RHS 146A. Lower surface: RHS 146B with purplish-red edge (RHS N77A). Texture (both upper and lower surfaces): Smooth. Thickness: 2.0 mm to 3.0 mm. Variegation: Absent. Venation: Pattern: Parallel. Color of the midvein: Upper surface: RHS 146A. Lower surface: Yellow-green (RHS 144A) at the base and purple (RHS N77A) toward the tip.

Peduncle:

*Quantity per plant*.—1 to 2.

*Number of flowers per peduncle*.—9 to 13.

*Length*.—55.0 cm to 60.0 cm.

*Diameter*.—5.6 mm to 6.1 mm.

*Strength*.—Strong.

*Aspect*.—Upright to slightly pendant.

*Texture*.—Smooth.

*Color*.—Mix of brown (RHS 200A) and yellow-green (RHS 146C).

*Internode length*.—3.5 cm to 4.5 cm.

Inflorescence description:

*Appearance*.—Upright to slightly pendant, raceme or panicle inflorescence with bilaterally symmetrical flowers that open in succession beginning with the lowermost flower.

*Number of inflorescences*.—1 to 2.

*Inflorescence size*.—Height (from base to tip): 200.0 mm to 240.0 mm.

*Flowering time*.—First flowers can be expected 10 to 11 months after planting in a 12-cm pot.

*Flower*.—Height: 73.0 mm to 78.0 mm. Diameter: 93.0 mm to 98.0 mm. Depth of lip: 30.0 mm to 32.0 mm.

*Flower longevity*.—On the plant: 6 to 8 weeks.

*Flower shape*.—Flat.

*Fragrance*.—Absent.

*Flower bud*.—Average size: Large. Length: 22.0 mm to 24.0 mm. Width: 20.0 mm to 22.0 mm. Shape: Egg shaped. Color: Dark purplish-red (RHS N79C).

*Petals*.—Arrangement: Open/free. Shape: Semi-circular. Apex: Emarginated asymmetric. Margin: Moderately undulated. Length (from base to tip): 43.0 mm to 45.0 mm. Width: 56.0 mm to 58.0 mm. Position of the broadest part of the petal: Toward the base. Color (when fully opened): Upper surface: Basic color: Reddish-purple (between RHS N78A and NN78A). Over color: Very light purple edge (RHS 76B). Lower surface: Basic color: Reddish-purple (RHS N78B). Over color: Light purple (RHS 76A) at the base and edge. Number of spots and stripes on the petals (upper surface): Few very small spots at the base. Color of spots and stripes on the petals (upper surface): RHS 76B. Density of netting of the petals (upper surface): None. Color of the netting (upper surface): None.

*Dorsal sepal*.—Shape: Elliptic. Apex: Obtuse symmetric. Margin: Entire. Length (from base to tip): 42.0 mm to 44.0 mm. Width: 29.0 mm to 31.0 mm. Position of the broadest part of the dorsal sepals: In the middle. Color (when fully opened): Upper surface: Basic color: Purplish-red (RHS 72A). Over color: Absent. Lower surface: Basic color: Reddish-purple (RHS N78B). Over color: Purplish-pink (RHS N78C). Number of spots and stripes on the dorsal sepals (upper surface): Many very small spots and medium stripes. Color of spots and stripes on the dorsal sepals (upper surface): Spots: RHS 76B; stripes: RHS N79C. Density of netting of the dorsal sepals (upper surface): None. Color of the netting (upper surface): None.

*Lateral sepals*.—Shape: Ovate. Apex: Obtuse symmetric. Margin: Entire. Length (from base to tip): 45.0 mm to 47.0 mm. Width: 27.0 mm to 29.0 mm. Position of the broadest part of the lateral sepals: At the base. Color (when fully opened): Upper surface: Basic color: Dark reddish-purple (RHS 72A). Over color: Slightly light green (RHS 195A) and red (RHS 60A) at the base. Lower surface: Basic color: Reddish-purple (RHS 72B). Over color: Touch of yellow-green (RHS 195B) at the base and reddish-purple middle vein (RHS N78B). Number of spots and stripes on the lateral sepals (upper surface): Very many very small dots and medium stripes. Color of spots and stripes on the lateral sepals (upper surface): Dots: RHS 60A at the base and RHS 60A toward the tip; stripes: RHS N79C. Density of netting of the lateral sepals (upper surface): None. Color of the netting (upper surface): None.

*Labellum* (*lip*).—Whiskers: Present. Length of whiskers: 9.0 mm to 11.0 mm. Color of whiskers: Dark purplish-red (RHS N79C) with white tips (RHS NN155C). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Entire. Length: 19.0 mm to 21.0 mm. Width: 14.0 mm to 16.0 mm. Color: Upper surface: Slightly yellow (RHS 8A) at the base; red (RHS 60A) toward the middle of the lobe and reddish-purple (RHS N78A) toward the edge. Lower surface: Yellowish-white (RHS 156D) at the base on one side; reddish (RHS 60A) on the other side; reddish-purple (RHS N78B) toward the tip. Number of spots and stripes on the lateral lobe (upper surface): Few stripes at the base. Color of spots and stripes on the lateral lobe (upper surface): RHS 60A. Density of netting of the lateral lobe (upper surface): None. Color of the netting (upper surface): None.

*Apical lobe*.—Shape: Triangular. Margin: Entire. Length: 19.0 mm to 21.0 mm. Width: 17.0 mm to 19.0 mm. Color: Upper surface: Red-purple wings (RHS 60A and 72A); reddish-purple (mix of RHS N78A and NN78A) toward the whiskers. Lower surface: Purplish-red (RHS 71A) at the base and wings; reddish-purple (RHS N78A) toward edge; purplish-pink (RHS N78C) in the middle. Number of spots and stripes on the apical lobe (upper surface): None. Color of spots and stripes on the apical lobe (upper surface): None. Density of netting of the apical lobe (upper surface): None. Color of the netting (upper surface): None.

*Callus*.—Average size: Medium to large. Height: 7.0 mm to 8.0 mm. Length: 6.0 mm to 7.0 mm. Width: 4.0 mm to 5.0 mm. Color: Purplish-red (RHS 70A) at the base; light yellow (RHS 10B) with reddish spots (RHS 184B).

Reproductive organs:

*Column*.—Length: 7.0 mm to 9.0 mm. Diameter: 5.0 mm to 6.0 mm. Color: Reddish-purple (RHS N78A).

*Pollinia*.—Quantity: 2. Diameter: 0.9 mm to 1.2 mm. Color: Orange (RHS 25A).

*Ovary*.—Length: 11.0 mm to 13.0 mm. Diameter: 2.0 mm to 3.0 mm.

*Pedicel*.—Length: 34.0 mm to 36.0 mm. Diameter: 3.0 mm to 4.0 mm. Texture: Smooth. Color: Mix of brown (RHS 200D) and green (RHS 147C) at the base; light reddish-purple (RHS N78D) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

The female parent plant of 'PHALHITWOQ', cultivar '32522-04' (unpatented), is no longer in existence, so a meaningful comparison cannot be made.

'PHALHITWOQ' differs from male parent plant '32522-03' (unpatented) in that 'PHALHITWOQ' has petals in an open/free arrangement with emarginated apexes, whereas '32522-03' has petals that are touching with rounded apexes.

'PHALHITWOQ' is most similar to the commercial *Phalaenopsis* plants named 'PHALOSZIH' (U.S. Plant Pat. No. 29,945) and 'PHALGLAOR' (U.S. Plant patent application Ser. No. 16/501,177). 'PHALHITWOQ' differs from the commercial variety 'PHALOSZIH' in that 'PHALHITWOQ' has emarginated petal apexes, whereas 'PHALOSZIH' has rounded petal apexes. Additionally, 'PHALHITWOQ' has longer lateral sepals than 'PHALOSZIH'.

'PHALHITWOQ' differs from the commercial variety 'PHALGLAOR' in that 'PHALHITWOQ' has emarginated petal apexes, whereas 'PHALGLAOR' has rounded to slightly mucronated petal apexes. Additionally, 'PHALHITWOQ' has shorter whiskers and narrower apical lobes than 'PHALGLAOR'.

I claim:

1. A new and distinct variety of *Phalaenopsis* plant named 'PHALHITWOQ', substantially as described and illustrated herein.

* * * * *